(12) United States Patent
Shah et al.

(10) Patent No.: US 8,206,728 B2
(45) Date of Patent: Jun. 26, 2012

(54) SUNSCREEN COMPOSITIONS CONTAINING FLUORINATED ALKYL ETHERS

(75) Inventors: Anil Shah, East Windsor, NJ (US); Isabelle Hansenne, Westfield, NJ (US); Angelike Galdi, Westfield, NJ (US)

(73) Assignee: L'Oréal (FR)

( * ) Notice: Subject to any disclaimer, the term of this patent is extended or adjusted under 35 U.S.C. 154(b) by 761 days.

(21) Appl. No.: 10/991,937

(22) Filed: Nov. 18, 2004

(65) Prior Publication Data

US 2006/0104923 A1    May 18, 2006

(51) Int. Cl.
   *A61K 8/02*     (2006.01)
   *A61K 8/00*     (2006.01)
   *A61K 8/70*     (2006.01)

(52) U.S. Cl. .............. 424/401; 424/59; 514/759

(58) Field of Classification Search .............. None
See application file for complete search history.

(56) References Cited

U.S. PATENT DOCUMENTS

| | | | |
|---|---|---|---|
| 4,193,989 A * | 3/1980 | Teng et al. | 424/60 |
| 4,686,099 A * | 8/1987 | Palinczar | 424/47 |
| 5,741,499 A | 4/1998 | Arnauld et al. | |
| 5,766,575 A * | 6/1998 | Crotty et al. | 424/59 |
| 5,919,441 A * | 7/1999 | Mendolia et al. | 424/78.08 |
| 6,132,746 A * | 10/2000 | Hasenoehrl et al. | 424/402 |
| 6,159,917 A | 12/2000 | Baran, Jr. et al. | |
| 6,224,851 B1 | 5/2001 | Bara | |
| 6,322,776 B1 * | 11/2001 | Ortega et al. | 424/59 |
| 6,419,909 B1 | 7/2002 | Lorant et al. | |
| 6,444,213 B1 | 9/2002 | Morita et al. | |
| 6,616,917 B2 * | 9/2003 | Lorant et al. | 424/59 |
| 6,706,678 B2 | 3/2004 | Bargaje et al. | |
| 6,727,218 B2 | 4/2004 | Bargaje et al. | |
| 6,746,680 B2 | 6/2004 | Morita et al. | |
| 2002/0051758 A1 * | 5/2002 | Cai et al. | 424/65 |
| 2002/0182240 A1 * | 12/2002 | Morita et al. | 424/401 |
| 2003/0013753 A1 * | 1/2003 | Aung-Din | 514/419 |
| 2003/0180338 A1 | 9/2003 | Arnaud et al. | |
| 2003/0228335 A1 | 12/2003 | Suess | |
| 2004/0120975 A1 | 6/2004 | Lahanas et al. | |
| 2004/0126336 A1 * | 7/2004 | Hansenne et al. | 424/59 |
| 2007/0025937 A1 * | 2/2007 | Fares et al. | 424/62 |

FOREIGN PATENT DOCUMENTS

| | | |
|---|---|---|
| EP | 0 196 904 A2 | 10/1986 |
| EP | 0953 331 A2 | 11/1999 |
| EP | 1 064 926 A1 | 1/2001 |
| FR | 2 777 454 A1 | 10/1999 |

OTHER PUBLICATIONS

Smith GJ, Miller IJ, Clare FJ, Diffey BL. "The Effect of UV Absorbing Sunscreens on the Reflectance and teh Consequent Protection of Skin." Photochemistry and Photobiology, 2002, 75(2): 122-125.*
RK Chaudhuri, C Hwang. "Self-Tanners: Formulating with Dihydroxyacetone." Cosmetics and Toiletries, vol. 116, No. 9, Sep. 2001, pp. 87-90, 92, and 94-96.*
TJ McIntosh. "Organization of Skin Stratum Corneum Extracellular Lamellae: Diffraction Evidence for Asymmetric Distribution of Cholesterol." Biophysical Journal, vol. 85, Sep. 2003, pp. 1675-1681.*
KY Lee, DT Ha. "Phase Separation Behavior of Three Common Alcohols with Methoxy-Nonafluorobutane or Ethoxy-Nonafluorobutane in Water." Can J. Civ. Eng., vol. 36 Issue 4, 2009, pp. 738-742.*
3M Material Safety Data Sheet (HFE-7200).
3M Material Safety Data Sheet (HFE-7500).
Ausimont, Material Specification (Fomblin HC/25).
L'Oreal, Matiere Premiere Codee (Fomblin HC/25).
Ciba, Material Safety Data Sheet (TINOGARD TT).
TINOGARD TT, TS, NOA-Feature.

* cited by examiner

*Primary Examiner* — Frederick Krass
*Assistant Examiner* — Isaac Shomer
(74) *Attorney, Agent, or Firm* — Lerner, David, Littenberg, Krumholz & Mentlik, LLP

(57) ABSTRACT

Disclosed are sunscreen compositions containing at least one sunscreen agent, a volatile solvent comprising a cosmetically acceptable lower alkanol, and a fluorinated alkyl ether, and methods of making and using same.

30 Claims, No Drawings

SUNSCREEN COMPOSITIONS CONTAINING FLUORINATED ALKYL ETHERS

BACKGROUND OF THE INVENTION

Compositions containing sunscreens are highly popular. One problem with such sunscreen-containing compositions, however, is the provision of a high Sun Protection Factor (SPF) (e.g., more than 30), especially when the composition contains alcohol. Ethanol, the most commonly used alcohol in such compositions, stabilizes the ground state of the composition. This inhibits the delocalization of the electrons in the active sunscreen agent, thereby reducing the absorbance thereof to a lower wavelength (i.e., below the wavelength of ultra violet light), which accordingly reduces the SPF of the composition.

The organic active sunscreen agent octocrylene is commonly used in sunscreen compositions. However, a common drawback to alcoholic sunscreen sprays containing octocrylene is that a strong celery odor is given off. This odor cannot be masked by fragrances, which are generally not preferable regardless of their ability to mask odors.

SUMMARY OF THE INVENTION

A first aspect of the present invention is directed to a sunscreen composition comprising at least one sunscreen agent; at least one volatile solvent comprising a cosmetically acceptable lower alkanol; and a fluorinated alkyl ether. Applicants have discovered that including a fluorinated alkyl ether in the composition (in place of a portion of the alkanol that would otherwise be present in such compositions) unexpectedly raises SPF value. Methods of applying the compositions to keratinous tissue and fibers are also provided.

A second aspect of the present invention is directed to a method of preparing a sunscreen composition comprising mixing together at least one sunscreen agent, at least one volatile solvent comprising a cosmetically acceptable lower alkanol, and a fluorinated alkyl ether.

A third aspect of the present invention is directed to a method of increasing the sun protection factor of a sunscreen composition, comprising preparing a composition comprising the sunscreen agent, a volatile solvent comprising a cosmetically acceptable lower alkanol, and a fluorinated alkyl ether.

A fourth aspect of the present invention is directed to a sunscreen composition comprising at least one sunscreen agent comprising a β,β-diphenylacrylate derivative (preferably octocrylene) and an anti-odor agent which is tetrabutyl ethylidinebisphenol, tetradibutyl pentaerithrityl hydroxyhydrocinnamate, or octadecyl di-t-butyl-4-hydroxyhydrocinnamate. The presence of such agents reduces the celery odor caused by these types of sunscreens. Methods of making and applying these compositions to keratinous tissue and fibers are also provided.

DETAILED DESCRIPTION

Fluorinated alkyl ethers (also termed hydrofluroethers) suitable for use in the present invention are generally low polarity chemical compounds minimally containing carbon, fluorine, hydrogen and catenary (i.e., in-chain) oxygen atoms. They are typically linear or branched, free of ethylenic unsaturation, and are monomeric in nature (i.e., as distinguished from hydrofluoropolyethers). Fluorinated alkyl ethers are available commercially, either as essentially pure compounds or as mixtures. Representative examples include methoxy-nonafluorobutane, which is commercially available under the name Novec® Engineered Fluid HFE-7100 from the 3M® Company; ethoxy-nonafluorobutane, which is commercially available under the names Novec® Engineered Fluid HFE-7200 or Cosmetic Fluid CF-76, both from the 3M® Company; and 2-trifluoromethyl 3-ethoxy dodecafluorohexane, which is commercially available under the name Novec® Engineered Fluid HFE-71IPA from the 3M® Company. HFE-7100 has a formula of $C_4F_9OCH_3$ and contains two inseparable isomers with essentially identical properties. These are $(CF_3)_2CFCF_2OCH_3$ (CAS No. 163702-08-7) and $CF_3CF_2CF_2CF_2OCH_3$ (CAS No. 163702-07-6) or methyl nonafluoroisobutyl ether and methyl nonafluorobutyl ether. HFE-71IPA is a hydrofluoroether in an azeotropic formulation with isopropanol, and is identical in composition to HFE-7100 except that it has isopropyl alcohol added in an amount of 4% to 6% by weight. The alcohol is added to the fluid to change its surface tension, density and wetting property. HFE-7200 has a formula of $C_4F_9OC_2H_5$ and contains two inseparable isomers with essentially identical properties. These are ethyl nonafluoroisobutyl ether, which has a formula of $(CF_3)_2CFCF_2OC_2H_5$ (CAS No. 163702-06-5) and ethyl nonafluorobutyl ether, which has a formula of $CF_3CF_2CF_2CF_2OC_2H_5$ (CAS No. 163702-05-4).

Preferably, the at least one fluorinated alkyl ether contains a perfluoroether of the general formula:

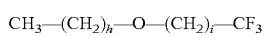

$$CH_3—(CH_2)_h—O—(CH_2)_i—CF_3$$

wherein h is an integer having a value of 0, 1, 2, or 3, and wherein i is an integer having a value of 2, 3, 4, or 5.

The amount of fluorinated alkyl ether is present in the compositions of the present invention in an amount generally ranging from about 5% to about 40%, and preferably from about 15% to about 35%, based on the total weight of the sunscreen composition. Applicants have found that the presence of the fluorinated alkyl ether in the composition in these amounts may effectively increase the SPF of the sunscreen by about 20% or more.

Sunscreen compositions of present invention also contain at least one volatile solvent that is a cosmetically acceptable lower alkanol, and preferably ethanol. Other suitable lower alkanols include isopropanol and butanol. Other volatile solvents may be present to the extent they are compatible with the lower alkanol. Additional solvents useful in the present invention include methyl ethyl ketone, tetrahydrofuran, methyl acetate, ethyl acetate, lower alkylene glycols e.g., polypropylene glycol, and glycol ethers. Volatile silicone oils may also be useful. Such oils include cyclic silicones having from 3 to 8 silicon atoms, e.g., cyclic silicones having 4 to 6 carbon atoms such as, for example cyclotetradimethylsiloxane, cyclopentadimethylsiloxane, or cyclohexadimethylsiloxane, and cyclocopolymers of the dimethylsiloxane/methylalkylsiloxane type, such as SILICONE FZ 3109, sold by Union Carbide, which is a dimethylsiloxane/methyloctylsiloxane cyclocopolymer, and linear silicones having from 2 to 9 silicon atoms, for example hexamethyldisiloxane, hexylheptamethyltrisiloxane, and octylheptamethyltrisiloxane. Mention may also be made of volatile hydrocarbonaceous oils, such as isoparaffins, including isododecane.

In general, the volatile solvent is present in an amount of about 30% to about 90%, and preferably about 30% to about 80%, and more preferably about 70%, based on the total weight of the composition. Due to the presence of the monomeric fluorinated alkyl ether, however, relatively less solvent can be used compared to the amount that would ordinarily be present in a sunscreen composition. For example, in an embodiment of the present invention, a mixture of volatile solvents comprising e.g., alcohol, and a fluorinated alkyl ether is present in an amount of about 70% of the total weight of the gel or spray sunscreen composition. While a typical sunscreen composition would contain the alcohol in that amount, in a composition according to the present invention, about 15 to 35% of the alcohol is replaced with a fluorinated alkyl ether such that the resulting composition contains about 35 to 55% of alcohol based on the total weight of the composition.

The sunscreen compositions of the present invention may contain water, but typically in amounts less than about 10% (e.g., 10%), and preferably not more than about 7% (e.g., 7%), based on the total amount of the sunscreen composition. In other embodiments, the compositions do not contain added water. Thus, the sunscreen compositions of the present invention may be said to be substantially anhydrous. The inventive compositions, therefore, are not emulsions.

Sunscreens useful in the present invention include organic sunscreens and/or inorganic sunscreens which are preferably active in the UV-A and/or UV-B regions (absorbers), and are soluble in water or in fats or insoluble in, e.g., cosmetic solvents commonly used. The sunscreens useful in the present invention preferably comprise chemical absorbers. Typically, the compositions of the present invention contain combinations of two or more sunscreens.

Organic sunscreens useful herein include anthranilates; cinnamic derivatives; dibenzoylmethane derivatives; salicylic derivatives; camphor derivatives; triazine derivatives, such as those disclosed in U.S. Pat. No. 4,367,390, EP 863 145, EP 517 104, EP 570 838, EP 796 851, EP 775 698, EP 878 469, EP 933 376, EP 507 691, EP 507 692, EP 790 243 and EP 944 624; benzophenone derivatives; β,β-diphenylacrylate derivatives; benzotriazole derivatives; benzalmalonate derivatives; benzimidazole derivatives; imidazolines; bisbenzoazolyl derivatives as disclosed in Patents EP 669 323 and U.S. Pat. No. 2,463,264; p-aminobenzoic acid (PABA) derivatives; methylenebis(hydroxyphenylbenzotriazole) derivatives as disclosed in U.S. Pat. Nos. 5,237,071 and 5,166,355, GB 2 303 549, DE 197 26 184 and EP 893 119; screening polymers and screening silicones, such as those disclosed in particular in WO 93/04665; dimers derived from α-alkylstyrene, such as those disclosed in DE 198 55 649; 4,4-diarylbutadienes as disclosed in EP 0 967 200, DE 197 46 654, DE 197 55 649, EP-A-1 008 586, EP 1133 980 and EP 133 981; and their mixtures.

More specifically, mention may be made, as sunscreens which are generally active in the UV-A and/or UV-B regions, denoted below under their INCI names, of: p-aminobenzoic acid (PABA) derivatives, in particular PABA, ethyl PABA, ethyl dihydroxypropyl PABA, ethylhexyl dimethyl PABA (sold in particular under the name "Escalol 507" by ISP), glyceryl PABA or PEG-25 PABA (sold under the name "Uvinul P25" by BASF), salicylic derivatives, in particular homosalate (sold under the name "Eusolex HMS" by Rona/EM Industries), ethylhexyl salicylate (sold under the name "Neo Heliopan OS" by Haarmann and Reimer), dipropylene glycol salicylate (sold under the name "Dipsal" by Scher), or TEA salicylate (sold under the name "Neo Heliopan TS" by Haarmann and Reimer), dibenzoylmethane derivatives, in particular butyl methoxydibenzoylmethane (sold in particular under the trade name "Parsol 1789" by Hoffmann-LaRoche), or isopropyl dibenzoylmethane, cinnamic derivatives, in particular ethylhexyl methoxycinnamate (sold in particular under the trade name "Parsol MCX" by Hoffmann-LaRoche), isopropyl methoxycinnamate, isoamyl methoxycinnamate (sold under the trade name "Neo Heliopan E 1000" by Haarmann and Reimer), cinoxate, DEA methoxycinnamate, diisopropyl methyl cinnamate, or glyceryl ethylhexanoate dimethoxycinnamate, β,β-diphenylacrylate derivatives, in particular octocrylene (sold in particular under the trade name "Uvinul N539" by BASF) or etocrylene (sold in particular under the trade name "Uvinul N35" by BASF), benzophenone, in particular benzophenone-1 (sold under the trade name "Uvinul 400" by BASF), benzophenone-2 (sold under the trade name "Uvinul D50" by BASF), benzophenone-3 or oxybenzone (sold under the trade name "Uvinul M40" by BASF), benzophenone-4 (sold under the trade name "Uvinul MS40" by BASF), benzophenone-5, benzophenone-6 (sold under the trade name "Helisorb 11" by Norquay), benzophenone-8 (sold under the trade name "Spectra-Sorb WV-24" by American Cyanamid), benzophenone-9 (sold under the trade name "Uvinul DS-49" by BASF), benzophenone-12, or n-hexyl 2-(4-diethylamino-2-hydroxybenzoyl)benzoate, benzylidene camphor derivatives, in particular 3-benzylidene camphor (manufactured under the name "Mexoryl SD" by Chimex), 4-methylbenzylidene camphor (sold under the name "Eusolex 6300" by Merck), benzylidene camphor sulphonic acid (manufactured under the name "Mexoryl SL" by Chimex), camphor benzalkonium methosulphate (manufactured under the name "Mexoryl SO" by Chimex), terephthalylidene dicamphor sulphonic acid (manufactured under the name "Mexoryl SX" by Chimex), or polyacrylamidomethyl benzylidene camphor (manufactured under the name "Mexoryl SW" by Chimex), benzimidazole derivatives, in particular phenylbenzimidazole sulphonic acid (sold in particular under the trade name "Eusolex 232" by Merck), or disodium phenyl dibenzimidazole tetrasulphonate (sold under the trade name "Neo Heliopan AP" by Haarmann and Reimer) triazine derivatives, in particular anisotriazine (sold under the trade name "Tinosorb S" by Ciba Specialty Chemicals), ethylhexyl triazone (sold in particular under the trade name "Uvinul T150" by BASF), diethylhexyl butamido triazone (sold under the trade name "Uvasorb HEB" by Sigma 3V) or 2,4,6-tris(diisobutyl 4'-amino-benzalmalonate)-s-triazine-, benzotriazole derivatives, in particular drometrizole trisiloxane (sold under the name "Silatrizole" by Rhodia Chimie) or methylene bisbenzotriazolyl tetramethylbutylphenol (sold in the solid form under the trade name "Mixxim BB/100" by Fairmount Chemical or in the micronized form in aqueous dispersion under the trade name "Tinosorb M" by Ciba Specialty Chemicals), anthranilic derivatives, in particular menthyl anthranilate (sold under the trade name "Neo Heliopan MA" by Haarmann and Reimer), imidazoline derivatives, in particular ethylhexyl dimethoxybenzylidene dioxoimidazoline propionate, benzalmalonate derivatives, in particular polyorganosiloxane comprising benzalmalonate functional groups (sold under the trade name "Parsol SLX" by Hoffmann-LaRoche), and 4,4-diarylbutadiene derivatives, in particular 1,1'-dicarboxy (2,2'-dimethylpropyl)-4,4-diphenylbutadiene, and their mixtures.

Organic sunscreens which are useful herein include ethylhexyl salicylate, ethylhexyl methoxycinnamate, octocrylene, phenylbenzimidazole sulphonic acid, benzophenone-3, benzophenone-4, benzophenone-5, 4-methylbenzylidene camphor, terephthalylidene dicamphor sulphonic acid, disodium phenyl dibenzimidazole tetrasulphonate, 2,4,6-tris(diisobutyl 4'-aminobenzalmalonate)-s-triazine, anisotriazine, ethylhexyl triazone, diethylhexyl butamido triazone, methylene bisbenzotriazolyl tetramethylbutylphenol, drometrizole trisiloxane, 1,1'-dicarboxy(2,2'-dimethylpropyl)-4,4-diphenylbutadiene, and their mixtures.

Representative inorganic sunscreens include pigments or alternatively nanopigments (mean size of the primary particles: generally between 5 nm and 100 nm, preferably between 10 nm and 50 nm) formed from coated or uncoated metal oxides, such as, for example, titanium oxide (amorphous or crystalline in the rutile and/or anatase form), iron oxide, zinc oxide, zirconium oxide or cerium oxide nanopigments, which are all known in the art as UV sunscreens. Conventional coating agents are, furthermore, alumina and/or aluminium stearate. Such nanopigments formed from coated or uncoated metal oxides are disclosed in particular in EP 518 772 and EP 518 773.

Another group of sunscreens useful in the present invention are certain UV-A and UV-B absorbers. Classifying the chemical absorbers generally as UV-A or UV-B absorbers is accepted within the industry. However, a more precise classification is one based upon the chemical properties of the sunscreens. There are eight major classifications of sunscreen chemical properties that are discussed at length in "Sunscreens—Development, Evaluation and Regulatory Aspects," by N. Shaath, et al., 2nd. Edition, pages 269-273, Marcel Dekker, Inc. (1997). This discussion, in its entirety, is incorporated by reference herein.

Preferred UV-A absorbers generally absorb radiation in the 320 to 400 nm region of the ultraviolet spectrum. Such preferred UV-A absorbers include anthranilates, benzophenones, and dibenzoyl methanes. Preferred UV-B absorbers generally absorb radiation in the 280 to 320 nm region of the ultraviolet spectrum. Such preferred UV-B absorbers include p-aminobenzoic acid derivatives, camphor derivatives, cinnamates, and salicylates. Other sunscreens active in the UV-A and/or UV-B range include:
p-aminobenzoic acid;
oxyethylene (25 mol) p-aminobenzoate;
2-ethylhexyl p-dimethylaminobenzoate;
ethyl N-oxypropylene p-aminobenzoate;
glycerol p-aminobenzoate;
4-isopropylbenzyl salicylate;
2-ethylhexyl 4-methoxycinnamate;
methyl diisopropylcinnamate;
isoamyl 4-methoxycinnamate;
diethanolamine 4-methoxycinnamate;
3-(4'-trimethylammunium)-benzyliden-bornan-2-one methylsulfate;
2-hydroxy-4-methoxybenzophenone;
2-hydroxy-4-methoxybenzophenone-5-sulfonate;
2,4-dihydroxybenzophenone;
2,2',4,4'-tetrahydroxybenzophenone;
2,2'-dihydroxy-4,4'dimethoxybenzophenone;
2-hydroxy-4-n-octoxybenzophenone;
2-hydroxy-4-methoxy-4'-methoxybenzophenone;
-(2-oxoborn-3-ylidene)-tolyl-4-sulfonic acid and soluble salts thereof;
3-(4'-sulfo)benzyliden-bornan-2-one and soluble salts thereof;
3-(4'methylbenzylidene)-d,1-camphor;
3-benzylidene-d,1-camphor;
benzene 1,4-di(3-methylidene-10-camphosulfonic) acid and salts thereof (the product Mexoryl SX described in U.S. Pat. No. 4,585,597);
urocanic acid;
2,4,6-tris[p-(2'-ethylhexyl-1'-oxycarbonyl)-anilino]-1,3,5-triazine-,
2-[(p-(tertiobutylamido)anilino]-4,6-bis-[(p-(2'-ethylhexyl-1'-oxycarbonyl)anilino]-1,3,5-triazine;
2,4-bis{[4-(2-ethyl-hexyloxy)]-2-hydroxy]-phenyl}-6-(4-methoxy-phenyl)-1,3,5-triazine ("TINOSORB S" marketed by Ciba);
the polymer of N-(2,4)-[(2-oxoborn-3-yliden)methyl]benzyl]-acryl-amide;
1,4-bisbenzimidazolyl-phenylen-3,3',5,5'-tetrasulfonic acid and salts thereof;
the benzalmalonate-substituted polyorganosiloxanes;
the benzotriazole-substituted polyorganosiloxanes (Drometrizole Trisiloxane);
dispersed 2,2'-methylene-bis-[6-(2H-benzotriazol-2-yl)-4-(1,1,3,3-tetramethylbutyl)phenol] such as that marketed under the trademark MIXXIM BB/100 by Fairmount Chemical, or micronized in dispersed form thereof such as that marketed under the trademark TINOSORB M by Cibα-Geigy; and
solubilized 2,2'-methylene-bis-[6-(2H-benzotriazol-2-yl)-4-(methyl)-phenol] such as that marketed under the trademark MIXXIM BB/200 by Fairmount Chemical.

The dibenzoyl methane derivatives other than avobenzone are described, for example, in FR-2,326,405, FR-2,440,933 and EP-0,114,607, hereby expressly incorporated by reference.

Other dibenzoyl methane sunscreens other than avobenzone include (whether singly or in any combination):
2-methyldibenzoylmethane;
4-methyldibenzoylmethane;
4-isopropyldibenzoylmethane;
4-tert.-butyldibenzoylmethane;
2,4-dimethyldibenzoylmethane;
2,5-dimethyldibenzoylmethane;
4,4'-diisopropyldibenzoylmethane;
4,4'-dimethoxydibenzoylmethane;
2-methyl-5-isopropyl-4'-methoxydibenzoylmethane;
2-methyl-5-tert-butyl-4'-methoxydibenzoylmethane;
2,4-dimethyl-4'-methoxydibenzoylmethane; and
2,6-dimethyl-4-tert-butyl-4'-methoxydibenzoylmethane.

Particularly useful sunscreens which may be formulated into the compositions of the present invention include chemical absorbers such as p-aminobenzoic acid derivatives, anthranilates, benzophenones, camphor derivatives, cinnamic derivatives, dibenzoyl methanes (such as avobenzone also known as Parsol® 1789), diphenylacrylate derivatives, salicylic derivatives, triazine derivatives, benzimidazole compounds, bis-benzoazolyl derivatives, methylene bis-(hydroxyphenylbenzotriazole) compounds, the sunscreen polymers and silicones, or mixtures thereof. These are variously described in U.S. Pat. Nos. 2,463,264, 4,367,390, 5,166,355 and 5,237,071 and in EP-0,863,145, EP-0,517,104, EP-0, 570,838, EP-0,796,851, EP-0,775,698, EP-0,878,469, EP-0, 933,376, EP-0,893,119, EP-0,669,323, GB-2,303,549, DE-1, 972,184 and WO-93/04665, all of which are also expressly incorporated herein by reference. Also exemplary of the sunscreens which may be formulated into the compositions of this invention are physical blockers such as cerium oxides, chromium oxides, cobalt oxides, iron oxides, red petrolatum, silicone-treated titanium dioxide, titanium dioxide, zinc oxide, and/or zirconium oxide, or mixtures thereof.

A wide variety of sunscreens, all of which are useful herein, are further described in U.S. Pat. Nos. 5,087,445 and 5,073,372; and Chapter VIII of *Cosmetics and Science and Technology*, by Segarin, et al., pages 189 et seq. (1957), all of which are incorporated herein by reference in their entirety.

Further sunscreens which may be formulated into the compositions of the instant invention are those selected from among: aminobenzoic acid, amyldimethyl PABA, cinoxate, diethanolamine p-methoxycinnamate, digalloyl trioleate, dioxybenzone, 2-ethoxyethyl p-methoxycinnamate, ethyl 4-bis(hydroxypropyl)aminobenzoate, 2-ethylhexyl-2-cyano-3,3-diphenylacrylate, ethylhexyl p-methoxycinnamate, 2-ethylhexyl salicylate, glyceryl aminobenzoate, homomenthyl salicylate, homosalate, 3-imidazol-4-ylacrylic acid and ethyl ester, methyl anthranilate, octyldimethyl PABA, 2-phenylbenzimidazole-5-sulfonic acid and salts, red petrolatum, sulisobenzone, titanium dioxide, triethanolamine salicylate, N,N,N-trimethyl-4-(2-oxoborn-3-ylidene methyl)anillinium methyl sulfate, and mixtures thereof.

Additional sunscreens that can be used herein are described in pages 2954-2955 of the *International Cosmetic Ingredient Dictionary and Handbook* (9th ed. 2002).

Preferred sunscreens are organic sunscreen agents. In particular, the use of monomeric fluorinated alkyl ether in a sunscreen composition containing the active sunscreen agent octocrylene is particularly advantageous.

Typically, the at least one sunscreen agent is present in an amount ranging from about 2 to about 20% of the total weight of the composition, preferably, about 5 to about 15%, and more preferably about 10% of the total weight of the composition. Since the presence of the fluorinated alkyl ether increases SPF value, relatively less active sunscreen agent is needed compared to similar compositions that do not include a fluorinated alkyl ether. Thus, sunscreen compositions of the present invention may contain as much as 30% less sunscreen agent in order to achieve the same SPF value.

The sunscreen compositions of the present invention are typically formulated in the form of a gel or a spray in accordance with standard procedures. Gels are obtained using gelling agents such as cellulose derivatives (e.g., ethyl cellulose and hydroxylpropyl cellulose), carboxyvinyl polymers (Carbopols), natural or synthetic gums, modified clays (bentones), metal salts of fatty acids (aluminum stearate), ethylene/acrylate copolymers, silicas and polyethylenes. Dow Corning® (DC) 2-8178 Gellant (a Nylon-611/dimethicone copolymer) is a preferred gelling agent. The gelling agent is typically used in an amount of about 0.5 and about 15%, based on the total weight of the composition.

Suitable spray compositions are well known in the art and include conventional, non-aerosol pump sprays, e.g., "atomizers," aerosol containers or cans having propellant, as well as pump aerosol containers utilizing compressed air as the propellant. Pump aerosol containers are disclosed, for example, in U.S. Pat. Nos. 4,077,441 and 4,850,517, both incorporated herein by reference.

Aerosol sprays can also include any of the conventional propellants to deliver the material, in a fine, uniform spray. Examples of suitable propellants include materials such as hydrofluorinated compounds, dichlorodifluoromethane, difluoroethane, dimethylether, isobutane, n-butane, propane, or trichlorofluoromethane. Water may be present in spray compositions of the present invention.

In some embodiments of the present invention, an artificial tanning agent is included in the sunscreen composition. A wide variety of artificial tanning agents have been developed. Artificial tanners provide the highly sought-after tanning or darkening response once only available through harmful exposure to ultraviolet radiation. DHA, in particular, has been widely utilized in cosmetics to accomplish artificial tanning of the skin via its interaction with proteins of the epidermis that have a very high concentration of arginine, lysine, and histidine. The tanning reaction involves combination with free amino groups in skin proteins, and particularly by combination of DHA with the free guanido group in arginine residues.

Preferred artificial tanners include allose, alpha hydroxy substituted ketones such as dihydroxyacetone, altrose, arabinose, erythrose, fructose, galactose, glucose, glyceraldehyde, indoles, lactose, mannose, threose, ribose, pentose, sucrose, tallose, xylose, and mixtures thereof.

Compositions of the present invention may further contain conventional cosmetic additives. Among these, mention may be made, for example, of preserving agents, antioxidants, film-forming polymers, soluble dyes and vitamins.

Another aspect of the present invention relates to compositions containing a sunscreen agent comprising a β,β-diphenylacrylate derivative (preferably octocrylene), and an antioxidant selected from tetrabutyl ethylidinebisphenol, tetradibutyl pentaerithrityl hydroxylhydrocinnamate, octadecyl di-t-butyl-4-hydroxyhydrocinnamate, and mixtures of two or more thereof. These compounds are oil-soluble phenolic antioxidants and are commercially available from Ciba under the tradenames TINOGARD NOA, TINOGARD TS and TINOGARD TT, respectively. These agents are present in amounts generally ranging from about 0.01% to about 0.1%, and preferably about 0.02% based on the total weight of the compositions. The presence of such agents reduces the celery odor that is characteristic of these types of sunscreens, and particularly octocrylene. The compositions also contain a volatile solvent, preferably ethanol, and optionally other cosmetically acceptable ingredients as described herein. Amounts of the sunscreen agent, solvent and other ingredients are disclosed supra, in connection with other inventive sunscreen compositions.

Compositions of the present invention may be applied to keratinous tissue or fibers (e.g., skin, hair, scalp) in accordance with known techniques.

The following examples are intended to further illustrate certain embodiments of the invention and are not intended to limit the invention in any way. Unless otherwise indicated, all percentages are weight-by-weight.

EXAMPLES

Example 1

Preparation of Clear Alcoholic Sunscreen Gel Using Ethoxy-Nonafluorobutane

TABLE 1

| Phase | Chemical Name | % Weight |
|---|---|---|
| A-1 | SD-Alc 40-2 (denatured alcohol) | 35.000 |
| A-1 | Octyldodecyl Neopentanoate | 5.000 |
| A-1 | C12–15 Alkyl Benzoate | 3.000 |
| A-1 | Avobenzone | 3.000 |
| A-1 | Octocrylene | 10.000 |
| A-1 | Octyl Salicylate | 5.000 |
| A-2 | DC Gellant 2-2178 | 2.000 |
| A-3 | Ethoxy-Nonafluorobutane | 35.000 |
| A-4 | Hydroxypropyl Cellulose | 2.000 |

The chemicals of table 1 were added together to form an anhydrous sunscreen composition in the form of a gel. The components of Phase A-1 were weighed into a beaker and stirred using an overhead mixer until all components were dissolved into the SD-Alc 40-2. The component of Phase A-2 was added into the Phase A-1 mixture until dissolved. Next, the component of Phase A-3 was added into the Phase A-1 and Phase A-2 mixture until dissolved. Finally, the component of Phase A-4 was slowly added into the above mixture while the stirring rate was increased. Mixing was continued for 1.5 to 2.0 hours.

Example 2

Preparation of Clear Alcoholic Sunscreen Spray Using Ethoxy-Nonafluorobutane

TABLE 2

| Phase | Chemical Name | % Weight |
|---|---|---|
| A-1 | SD-Alc 40-2 | 39.360 |
| A-1 | Water | 5.140 |
| A-2 | Dermacryl LT (film former) | 1.500 |
| B | Octyldodecyl Neopentanoate | 5.000 |
| B | Avobenzone | 3.000 |
| B | Octocrylene | 10.000 |
| B | Octyl Salicylate | 5.000 |
| B | Phenyltrimethicone | 1.000 |
| A-3 | Ethoxy-Nonafluorobutane | 30.000 |

A1 components were added to the main kettle, while mixing with a propeller. A2 ingredient was sprinkled into the vortex of A1, while mixing until clear. The components of phase B were added to a separate beaker and heated until they were completely dissolved and homogeneous, followed by cooling to room temperature. Phase B was then added to the main kettle, while mixing with a propeller for 5 minutes. Phase A3 was then added to the main kettle, while mixing with a propeller for 5 minutes. The final product was clear.

Example 3

Comparison of SPF of Alcoholic Sunscreen

TABLE 3

| | SPF (in-vitro) Result | | | |
|---|---|---|---|---|
| Composition | Batch 1 | Batch 2 | Batch 3 | Average |
| Sunscreen gel without ethoxy-nonafluorobutane | 27.44 | 21.15 | 25.69 | 24.76 |
| Sunscreen gel with 35% ethoxy-nonafluorobutane | 36.0 | 32.12 | 30.68 | 32.93 |

Gel Compositions

Two sunscreen compositions were compared—one which was the composition illustrated in Example 1, and a second that differed in that it did not contain ethoxy-nonafouorobutane, but rather SD-Alc 40-2 in an amount by weight equal to the total weight of SD-Alc 40-2 and ethoxy-nonafluorobutane of the composition of Example 1. Each of the compositions was made in three separate batches and the SPFs of the compositions were tested. As shown in Table 3, the inventive composition containing 35% ethoxy-nonafluorobutane had an average SPF that was 33% greater than the average SPF of the composition containing no ethoxy-nonafluorobutane.

Example 4

Comparison of SPF of Alcoholic Sunscreen Spray Compositions

TABLE 4

| | SPF (in-vitro) Result | | | |
|---|---|---|---|---|
| Composition | Batch 1 | Batch 2 | Batch 3 | Average |
| Sunscreen spray without ethoxy-nonafluorobutane | 18.59 | 16.37 | 17.91 | 17.62 |
| Sunscreen spray with 10% ethoxy-nonafluorobutane | 22.49 | 20.54 | 19.08 | 20.70 |
| Sunscreen spray with 20% ethoxy-nonafluorobutane | 22.88 | 20.97 | 19.72 | 21.19 |
| Sunscreen spray with 30% ethoxy-nonafluorobutane | 21.78 | 20.21 | 21.1 | 21.03 |

Three inventive sunscreen compositions were compared to sunscreen composition without fluorinated alkyl ether. First, an alcoholic sunscreen spray composition was made according to the procedure of Example 2. In addition, two alcoholic sunscreen spray compositions similar to that of Example 2 were also prepared having ethoxy-nonafluorobutane in amounts of 20% and 10% by weight. The amount of SD-Alc 40-2 in these compositions also varied (i.e., it was present in an amount of 35% or 70%). A fourth alcoholic sunscreen spray composition was made according to known methods. This composition was identical to the composition illustrated in Example 2, except that the composition did not contain ethoxy-nonafouorobutane, but rather SD-Alc 40-2 in an amount by weight equal to the total weight of SD-Alc 40-2 and ethoxy-nonafluorobutane of the composition of Example 2. Each of the compositions was made in three separate batches and the SPF's of the compositions were tested using the in vitro method described by B. L. Diffey, et al., J. Soc. Cosmet. Chem. 40:127-133 (1989), and which entails determining the monochromatic protection factors every 5 nm over a wavelength range from 290 to 400 nm and calculating the protection factor according to a given mathematical equation. (See U.S. Pat. No. 6,375,936, the contents of which are incorporated by reference herein.)

As shown in Table 4, the three inventive compositions were shown to have an average SPF value greater than that of the control sunscreen composition. Specifically, the composition containing 30% ethoxy-nonafluorobutane had an average SPF that was 19.4% greater than the average SPF of the composition containing no ethoxy-nonafluorobutane. Similarly, the composition containing 20% ethoxy-nonafluorobutane had an average SPF that was 20.3% greater than the average SPF of the composition containing no ethoxy-nonafluorobutane. The composition containing 10% ethoxy-nonafluorobutane had an average SPF that was 17.4% greater than the average SPF of the composition containing no ethoxy-nonafluorobutane.

Example 5

Comparison of Sunscreen Spary SPF 15, with and without Antioxident

| Phase | Chemical Name | % wt/wt |
|---|---|---|
| A-1 | SD-Alc 40-2 | 69.360% |
|  | Water | 5.140% |
| A-2 | DERMACRYL LT | 1.500% |
| B | Octyldodecyl Neopentanoate | 5.000% |
|  | Avobenzone | 3.000% |
|  | Octocrylene | 10.000% |
|  | Octyl Salicylate | 5.000% |
| C | Phenyl Trimethicone | 1.000% |
| A-1 | SD-Alc 40-2 | 69.260% |
|  | Water | 5.140% |
| A-2 | DERMACRYL LT | 1.500% |
| B | Octyldodecyl Neopentanoate | 5.000% |
|  | Avobenzone | 3.000% |
|  | Octocrylene | 10.000% |
|  | Octyl Salicylate | 5.000% |
|  | Tinogard TT | 0.100% |
| C | Phenyl Trimethicone | 1.000% |

A1 components were added to the main kettle, while mixing with a propeller. A2 ingredient was sprinkled into the vortex of A1, while mixing until clear. The components of phase B were added to a separate beaker and heated until they were completely dissolved and homogeneous, followed by cooling to room temperature. Phase B was then added to the main kettle, while mixing with a propeller for 5 minutes. Phase A3 was then added to the main kettle, while mixing with a propeller for 5 minutes. The final product was clear. The compositions were tested after several weeks of storage. When tested after 5 weeks of storage, the composition containing the antioxidant TINOGARD TT was found to have a relatively pleasant fragrance.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A sunscreen composition comprising:
at least one sunscreen agent selected from the group consisting of octocrylene, avobenzone, octyl salicylate, 2-hydroxy-4-methoxybenzophenone, and homosalate;
at least one volatile solvent;
at least one fluorinated alkyl ether selected from the group consisting of methoxy-nonafluorobutane and ethoxy-nonafluorobutane, wherein the fluorinated alkyl ether is present in the sunscreen composition in an amount from about 10% to about 35% by weight, based on the total weight of the composition; and
optionally water, in an amount no more than about 10% by weight;
wherein said sunscreen composition is not an emulsion and wherein the SPF of the sunscreen composition is higher than that of the same composition not containing said fluorinated alkyl ether.

2. The composition of claim 1, wherein said sunscreen agent is octocrylene.

3. The composition of claim 1, wherein the sunscreen agent comprises avobenzone.

4. The composition of claim 1, wherein the sunscreen agent comprises octyl salicylate.

5. The sunscreen composition of claim 1, wherein the sunscreen agent comprises 2-hydroxy-4-methoxybenzophenone.

6. The composition of claim 1, wherein said sunscreen agent is present in an amount of about 2% to about 20%, based on total weight of said composition.

7. The composition of claim 6, wherein the amount is about 5% to about 15%.

8. The composition of claim 1, wherein the volatile solvent comprises ethanol.

9. The composition of claim 1, wherein said volatile solvent is present in an amount of about 30% to about 90%, based on total weight of said composition.

10. The composition of claim 9, wherein said amount is about 30% to about 70%.

11. The composition of claim 1, further comprising a gelling agent.

12. The composition of claim 11, wherein said gelling agent comprises a Nylon-611/dimethicone copolymer.

13. The composition of claim 1, further comprising a propellant.

14. The composition of claim 13, further comprising water.

15. The composition of claim 14, wherein said water is present in an amount of about 7%, based on total weight of said composition.

16. The composition of claim 1, further comprising an artificial tanning agent.

17. The composition of claim 16, wherein said artificial tanning agent is dihydroxyacetone.

18. The composition of claim 1, comprising octocrylene, ethanol, methyl nonafluoroisobutyl ether and methyl nonafluorobutyl ether.

19. The composition of claim 1, comprising octocrylene, ethanol, ethyl nonafluoroisobutyl ether and ethyl nonafluorobutyl ether.

20. A method of increasing the sun protection factor of a sunscreen composition containing at least one sunscreen agent selected from the group consisting of octocrylene, avobenzone, octyl salicylate, 2-hydroxy-4-methoxybenzophenone, and homosalate; and at least one volatile solvent, comprising preparing a composition comprising the sunscreen agent, the volatile solvent, and at least one fluorinated alkyl ether selected from the group consisting of methoxy-nonafluorobutane and ethoxy-nonafluorobutane, wherein the fluorinated alkyl ether is present in the sunscreen composition in an amount from about 10% to about 35% by weight, based on the total weight of the composition and optionally water, in an amount no more than about 10% by weight;
wherein said sunscreen composition is not an emulsion, and wherein the SPF of the sunscreen composition is higher than that of the same composition not containing said fluorinated alkyl ether.

21. A method of preparing a sunscreen composition comprising mixing together at least one sunscreen agent selected from the group consisting of octocrylene, avobenzone, octyl salicylate, 2-hydroxy-4-methoxybenzophenone, and homosalate, at least one volatile solvent, and at least one fluorinated alkyl ether selected from the group consisting of methoxy-nonafluorobutane and ethoxy-nonafluorobutane, wherein the fluorinated alkyl ether is present in the sunscreen composition in an amount from about 10% to about 35% by weight, based on the total weight of the composition and optionally water, in an amount no more than about 10% by weight;

wherein said sunscreen composition is not an emulsion,
and wherein the SPF of the sunscreen composition is higher than that of the same composition not containing said fluorinated alkyl ether.

22. A method of protecting keratinous tissue or fibers from UV light, comprising applying to keratinous tissue or fibers the composition of claim 1.

23. The method of claim 22, wherein the composition is applied to skin.

24. The method of claim 22, wherein the composition is applied to scalp.

25. The method of claim 22, wherein the composition is applied to hair.

26. The sunscreen composition of claim 1, wherein the sunscreen agent comprises homosalate.

27. The sunscreen composition of claim 1, which is substantially anhydrous.

28. The composition of claim 1, wherein said methoxynonafluorobutane is a mixture of methyl nonafluoroisobutyl ether and methyl nonafluorobutyl ether.

29. The composition of claim 1, wherein said ethoxynonafluorobutane is a mixture of ethyl nonafluoroisobutyl ether and ethyl nonafluorobutyl ether.

30. The composition of claim 28, further comprising isopropanol.

* * * * *

UNITED STATES PATENT AND TRADEMARK OFFICE
CERTIFICATE OF CORRECTION

PATENT NO. : 8,206,728 B2  Page 1 of 1
APPLICATION NO. : 10/991937
DATED : June 26, 2012
INVENTOR(S) : Shah et al.

It is certified that error appears in the above-identified patent and that said Letters Patent is hereby corrected as shown below:

In the Specifications

Column 2, line 39, after "of", insert -- the --.

Column 10, line 46, "SPF's" should read -- SPFs --.

In the Claim

Claim 30, Column 14, line 11, "28" should read -- 1 --.

Signed and Sealed this
Seventh Day of January, 2014

Margaret A. Focarino
*Commissioner for Patents of the United States Patent and Trademark Office*